| United States Patent [19] | [11] 4,045,297 |
| Weeks et al. | [45] Aug. 30, 1977 |

[54] TRIGLYCERIDES DETERMINATION METHOD

[75] Inventors: Lloyd E. Weeks, St. Louis; John H. Johnson, Kirkwood; Margaret J. Reents, Manchester, all of Mo.

[73] Assignee: Monsanto Company, St. Louis, Mo.

[21] Appl. No.: 640,361

[22] Filed: Dec. 15, 1975

[51] Int. Cl.$^2$ .................................................. G01N 31/14
[52] U.S. Cl. ............................ 195/103.5 R; 204/1 T; 204/195 B
[58] Field of Search ............... 195/103.5 R; 204/1 E, 204/195 B

[56] References Cited

U.S. PATENT DOCUMENTS

| 3,703,591 | 11/1972 | Bucolo et al. | 195/103.5 R |
| 3,759,793 | 9/1973 | Stork et al. | 195/103.5 R |
| 3,862,009 | 1/1975 | Wahlefeld et al. | 195/103.5 R |
| 3,898,130 | 8/1975 | Komatsu | 195/103.5 R |

OTHER PUBLICATIONS

Greenbaum et al., "The Estimation of the Oxidized and Reduced Forms of the Nicotinamide Nucleotides," Biochem. J. 95 (1965), pp. 161–166.
Wieland, "Enzymatic Determination of Glycerol," Chemical Abstracts, vol. 52, (1958), No. 4732c.

*Primary Examiner*—Alvin E. Tanenholtz
*Assistant Examiner*—C. A. Fan
*Attorney, Agent, or Firm*—Scott J. Meyer; John D. Upham

[57] ABSTRACT

A method of determining triglycerides in biological fluids which comprises reacting a biological fluid sample with a lipolytic enzyme to liberate free glycerol, reacting said free glycerol with a coupled enzyme series in an oxygenated aqueous solution containing ATP, GK, α-GPDH, NAD and an electron transfer agent, and measuring the uptake of oxygen by the oxidation of the resulting NADH with an oxygen-sensing electrode.

7 Claims, No Drawings

TRIGLYCERIDES DETERMINATION METHOD

BACKGROUND OF THE INVENTION

This invention relates to a method for the determination of triglycerides. More particularly, this invention relates to a method for the determination of triglycerides in biological fluids with an oxygen-sensing electrode which measures dissolved oxygen in solution.

The triglycerides, or glycerol esters of fatty acids, are important water-insoluble substances found in plants and animals and comprise a major portion of the lipids in the human body. Although dietary fats and oils are the chief sources of lipids in the body, lipids are also synthesized in the body from nonlipid precursors. The importance of these fats in the diet can be attributed, in part, to the fact that they are the most concentrated of all food materials, furnishing about 9 calories of energy per gram as sources of heat and energy. Fats also promote the more efficient utilization of calories supplied by other foods, provide increased palatability and small amount of flavoring to other foods, and are vehicles for the fat-soluble vitamins A, D, E and K.

Digested fats are normally absorbed into the lymph through the duodenum and jejunum. About 100 grams of exogenous glycerides are absorbed by the intestinal mucosa daily in an average healthy person and transported as chylomicrons into the blood stream. Together with cholesterol and phospholipids, the triglycerides (neutral fats) constitute the principal lipids occurring in the blood.

Cholesterol, phospholipids and triglycerides are transported in the blood as macromolecules in combination with plasma globulins as lipoproteins, which also include the unesterified fatty acids bound to plasma albumin. An increase of any one or a combination of these lipids in the blood serum may undesirably increase the total lipids (hyperlipemia) whereas a decrease of the same may undesirably decrease the total lipids (hypolipemia).

In recent years, considerable attention has been given to the relationship between elevations of serum lipids and an increased risk of coronary artery disease and atherosclerosis. Since dietary and medical therapeutic means are now available to reduce serum lipid levels, methods for the determination of serum triglycerides are of significant clinical interest.

Historically, serum triglycerides have been determined generally by various macro- and micromethods such as described by Bloor, "Biochemistry of the Fatty Acids," ACS Monograph No. 93, Reinhold Publishing Company, New York, at pages 37-49 (1943). These procedures make use of the known phenomenon that triglycerides are readily soluble in the so-called fat solvents, for example, ether, petroleum ether, chloroform, carbon disulfide and carbon tetrachloride, but only sparingly soluble in alcohol. According to these procedures, the triglycerides are extracted from blood with the fat solvent, typically ether. Due to the presence of a high percentage of protein, it is generally necessary to follow the original ether extraction by extraction with alcohol followed by a second ether extraction. After extraction, the solvent is stripped by evaporation at low temperature, which leaves behind the remaining sample of triglycerides for examination and quantitation.

More recently, blood glycerol levels have been used as an index of lipolytic events in the body and various methods have been developed for determining these glycerol levels chromatographically, colorimetrically, enzymatically and fluorimetrically. In these procedures, the triglycerides are first saponified such as by alcoholic KOH and then the liberated glycerol is determined. In one typical procedure developed by Wieland, Biochem. Z.329, 313 (1957), glycerol is enzymatically converted by glycerokinase (GK) to α-glycerophosphate (α-GP) which, with α-glycerophosphate dehydrogenase (α-GPDH) and nicotinamide adenine dinucleotide (NAD), gives reduced nicotinamide adenine dinucleotide (NADH). The latter compound is then measured spectrophotometrically at 340 nm. A modification of this procedure described by Eggstein, Klin. Wscht. 44, 262 (1966), employs adenosine-5'-triphosphate (ATP), NADH, phosphoenolpyruvate (PEP), GK, pyruvate kinase (PK) and lactate dehydrogenase (LDH) in the system in which the decrease in NADH content is similarly measured spectrophotometrically. Yet another procedure reacts glycerol with NAD and glycerol dehydrogenase followed by spectrophotometric determination of the resulting NADH. These and similar such procedures are further described in Henry, "Clinical Chemistry, Principles and Technics", Harper and Row, Publishers 1964; Richterich, "Clinical Chemistry", Academic Press, Publishers 1969; Tietz, "Fundamentals of Clinical Chemistry," W.B. Saunders Company, Publishers 1970, and references cited therein.

SUMMARY OF THE INVENTION

In accordance with the present invention, a method is provided for the determination of triglycerides with an oxygen-sensing electrode system. The method involves the enzymatic hydrolysis of triglycerides followed by determination of liberated glycerol by means of a coupled enzyme series in which the uptake of dissolved oxygen by the oxidation of NADH is determined by an oxygen-sensing electrode. The rate of change in the electrode output is proportional to the concentration of glycerol. In addition to being a rapid, convenient and specific method for the determination of triglycerides, this method is free from interference by serum turbidity which frequently occurs with the usual spectrophotometric assay methods.

DETAILED DESCRIPTION OF THE INVENTION

In general, the method of the present invention comprises a two step assay procedure. The first step involves the hydrolysis of triglycerides by a lipolytic enzyme system while the second step involves the determination of the liberated glycerol by a coupled enzyme series of reactions. The sequence of reactions involved in the method can be illustrated as follows:

(1)

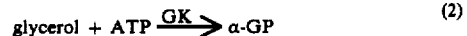

(2)

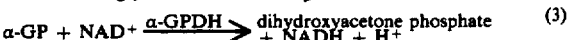

(3)

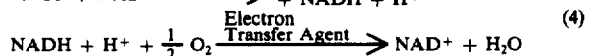

(4)

Following the hydrolysis in reaction (1), the coupled enzyme series of reactions (2), (3), and (4) proceeds to an equilibrium point in which the oxygen consumed is determined by an oxygen-sensing electrode.

The enzymatic hydrolysis of triglycerides has a distinct advantage over the saponification method for use with the oxygen-sensing electrode of the present invention. Thus, direct saponification of serum triglycerides has the disadvantage of releasing glycerol from phospholipids as well as from fats. It is necessary by such procedure to extract fats first and carry out saponification under anhydrous conditions, followed by acidification to layer out the free fatty acids produced. With the enzymatic hydrolysis as employed herein, the serum sample is incubated with the lipolytic enzyme to directly liberate glycerol which shows good correlation with theory based on comparison with control samples. No separation procedure is required in the present method.

Various lipolytic enzymes can be used in this hydrolysis step, including lipases and carboxylesterases. Suitable lipases can be obtained, for example, from animal and microbial sources such as pancreatic lipases and fungal lipases. Illustrative of the pancreatic lipases are Worthington pancreatic lipase obtained from the hog and having a pH optimum of 7-8.8, Pronase lipase which is commercially available from Calbiochem, and Fermlipase PL Concentrate from Fermco Labs.

Illustrative of the fungal lipases are those obtained from strains of Aspergillus, Candida, Mucor and Rhizopus, for example, *Aspergillus niger, A. flavus-oryzae, A. luchuensis, Candida lipolytica, C. cylindracea, C. paralipolytica, Mucor miehei, M. pusillus, M. lipolyticus, Rhizopus delemar, R. arrhizus,* and *R. nigricans.* The fungal lipases can be obtained by appropriate fermentation of the microorganism in nutrient culture media followed by recovery of the enzyme from the growth product by well-known methods as described, for example, in U.S. Pat. Nos. 2,480,090, 3,262,863 and 3,634,195. Lipase B from Rohm & Haas is an example of a typical commercially available fungal lipase.

Still other suitable lipases are lipoprotein lipase, steapsin, and pregastric lipases as described in U.S. Pat. Nos. 2,531,529 and 2,794,743. Carboxylesterases which can be used in the present invention are illustrated by acetyl esterase and acyl esterase.

The aforesaid enzymatic hydrolysis preferably is carried out with a combination of two lipase preparations, one being derived from *Candida cylindracea* and the other from *Rhizopus arrhizus.* These lipases are available commercially from Sigma Chemical Co. and Boehringer Mannheim Corp., respectively. Use of the combination of a carboxylesterase and a *Rhizopus arrhizus* lipase for triglyceride hydrolysis has been disclosed heretofore in German Offenlegunsschrift 2,229,849; whereas, use of the combination of a lipase from *Rhizopus delemar* and a protease such as chymotrypsin (which is known to have esterase activity) for triglyceride hydrolysis has been described previously by Bucolo and David, Clin. Chem. 19, 476-82 (1973) and in U.S. Pat. No. 3,703,591. Use of lipase from Candida cylindracea for the hydrolysis of triglycerides is taught in Japanese Pat. No. 71/16,509, Chem. Abstr. 76, 125614d. In accordance with the present invention, use of the aforesaid combination of lipase preparations from *Candida cylindracea* and *Rhizopus arrhizus* has been found to be more effective than use of the combination of either lipase with the protease chymotrypsin. Chymotrypsin causes undesirable drift with the oxygen-sensing electrode during the assay procedure.

The desired hydrolysis of the triglycerides as herein defined can be carried out by incubating the biological fluid sample, e.g., blood serum or plasma, with the lipolytic enzyme for about 10 to about 30 minutes at a temperature of from about 25° to about 40° C and at a pH of from about 7 to about 9, preferably at 30° C and pH 8. Incubation in a conventional buffer, for example, tris [tris(hydroxymethyl)aminomethane] buffer or glycine buffer, at the desired pH is suitable.

All of the chemical components required for the coupled enzyme series of reactions which follows the aforesaid triglyceride hydrolysis are available commercially. Thus, ATP is readily obtainable from mammalian skeletal muscle. It is usually isolated as the dibarium salt and for use is converted to the sodium or potassium salt. A synthetic route for its production is disclosed in U.S. Pat. No. 3,079,379.

Likewise, NAD is obtainable from animal muscle such as the rabbit and can also be isolated from bakers yeast or be prepared synthetically.

The glycerokinase (GK) and α-glycerophosphate dehydrogenase (α-GPDH) enzymes used in these reactions preferably should be in as pure a form as possible and should be free from trace amounts of glycerol. GK from Candida mycoderma and α-GPDH from rabbit muscle are examples of suitable products, both of which are commercially available from Sigma Chemical Co.

The kinase enzymatic reaction has an absolute cofactor requirement for $Mg^{++}$ ion for activity. This requirement can be provided by addition of a small but effective amount of a water soluble magnesium salt such as, for example, $MgSO_4$ and $Mg(C_2H_3O_2)_2$, to the enzyme substrate.

The oxidation reaction in which the reduced form of the coenzyme, NADH, is converted to the oxidized form, $NAD^+$, requires the presence of an electron transfer agent or electron acceptor. Useful electron transfer agents include, for example, methylene blue, meldola blue, and phenazine methosulfate. Of these electron transfer agents, phenazine methosulfate is preferred insofar as it produces a linear response over a more extended range of NADH concentration. Use of the phenazine methosulfate electron transfer agent in the estimation of the oxidized and reduced forms of nicotinamide nucleotides with an oxygen sensing electrode is described by Greenbaum et al, Biochem. J. 95, 161-66 (1965).

In carrying out the coupled enzyme series of reactions, the initially prepared glycerol substrate from the triglyceride hydrolysis is allowed to react with the ATP, GK, NAD, α-GPDH and the electron transfer agent in an oxygenated aqueous media buffered to a pH of from about 8 to about 10. Illustrative buffers for use in the coupled enzyme reaction series are conventional tris and glycine buffers. The required oxygenation of the aqueous media can be conveniently accomplished by saturating with air or oxygen.

The proportions of the substrate and the reaction reagents can vary widely and are adjusted to convenient levels based on laboratory needs and the expected range of triglycerides (converted to glycerol) in the biological samples to be analyzed. In general, use of about molar equivalent amounts of ATP and NAD with respect to the free glycerol in the biological sample and small but catalytically effective amounts of the GK and α-GPDH enzymes are suitable.

Incubation time and temperature conditions are not critical and can be varied to facilitate completion of the reactions. Usually, depending upon the concentration of glycerol, the end point is reached within about 3 to 6 minutes at incubation temperatures ranging from about 25° to 40° C.

The coupled enzyme reaction series is conveniently carried out in a cuvette or other such sample container with an attached oxygen electrode. An attached recorder for the electrode indicates the electrode output. The reaction equilibrium point at which the reaction reaches a maximum as indicated by the output in millivolts on the recorder trace is taken as the end point for the determination.

In general, the oxygen-sensing electrode employed in this invention comprises an anode, a cathode, an electrolyte solution, and means whereby the diffusion flow of oxygen through a semi-permeable membrane into the electrolyte is measured. The current output is a linear function of oxygen tension which in turn varies directly with the diffusion flow of oxygen.

Oxygen-sensing electrodes are well-known. The Clark $pO_2$ electrode described in U.S. Pat. No. 2,913,386 is typical. In this electrode, oxygen diffuses through a gas-permeable polymeric membrane and is reduced at a platinum cathode which is kept at a fixed potential with respect to a silver-silver chloride reference anode. Such electrodes have been used heretofore for the determination of blood glucose levels by measuring the oxygen uptake in a glucose oxidase enzyme catalyzed reaction. Illustrative of such use of the Clark $pO_2$ electrode are the report by Kunz and Stastny, Clin. Chem. 20, 1018–1022 (1974) and the review article by Gough and Andrade, Science 180, 380–84 (1973). Similar such use of an oxygen-sensing electrode for measuring the oxygen uptake in a cholesterol oxidase enzyme catalyzed reaction is disclosed in German Offenlegungsschrift 2,224,132.

Oxygen-sensing electrodes also are commercially available or can be prepared in the laboratory. One such suitable electrode, commercially available from Beckman Instruments, Inc., consists of a gold cathode which is separated by an epoxy coating from a tubular silver anode. An inner sensor body is housed in a plastic casing and comes into contact with the sample reagent solution only through a Teflon (duPont polytetrafluoroethylene) plastic membrane. As oxygen diffuses through this membrane, it is electrochemically reduced at the cathode by an applied potential of 0.8 volts. The reaction causes a current to flow between the anode and cathode which is proportional to the partial pressure of oxygen in the reagent sample.

An example of a suitable laboratory prepared oxygen-sensing electrode for measuring dissolved oxygen in solution is described by Johnson et al, Biotechnol. & Bioeng. 6, 457–68 (1964). This electrode has a silver cathode, a lead anode, an acetate buffer as an electrolyte, and a Teflon plastic membrane. The electrolyte is an aqueous solution containing 0.1 molar sodium acetate and 0.1 molar acetic acid, or a more concentrated solution containing 5 M acetic acid and 0.5 M sodium acetate. A modification of this electrode is described by Borkowski and Johnson, Biotechnol. & Bioeng. 9, 635–39 (1967), in which the electrolyte is an aqueous solution of 5 M acetic acid, 0.5 M sodium acetate, 0.1 M lead acetate and has a pH of about 3. In addition, a silicone rubber insulated filter of glass wool or nylon is inserted between the lead anode and silver cathode to prevent lead particles from dropping onto the silver cathode and eventually causing a short circuit. The electrode has a linear response from below 0.00002 to over 0.2 atmosphere of oxygen. In this electrode, the reaction at the silver cathode is believed to be $$(1/2) O_2 + H_2O + 2e^- \rightarrow 2OH^-$$

while at the lead anode the loss of electrons produces lead ions.

$$Pb \rightarrow Pb^{++} + 2e^-$$

The lead ions combine with hydroxyl to form lead hydroxide on the anode surface to result in an overall reaction as follows:

$$(1/2) O_2 + Pb + H_2O \rightarrow Pb(OH)_2$$

With acetate as the electrolyte, a deposit of basic lead acetate builds up on the lead surface and lead salts accumulate in the electrolyte. The expendable materials thereby are the lead anode and the acetate of the electrolyte.

A further modification of the above-described Johnson electrode is disclosed by Elsworth, The Chemical Engineer, February 1972, pp. 63–71.

Still other oxygen-sensing electrodes for use in the present invention are described in U.S. Pat. Nos. 3,449,231, 3,454,485 and 3,539,455.

Although Teflon plastic and silicone rubber have been specifically described above, it should be understood that other membrane materials permeable to oxygen and impermeable to water and electrolytes can be used in the oxygen-sensing electrode, for example, polyethylene, polypropylene, polystyrene, and polyvinyl chloride. Other suitable anode-cathode materials include, for example, any noble metal cathode such as gold, silver or rhodium in conjunction with a zinc, cadmium or lead anode.

In the instant invention, the diffusion flow of oxygen through the plastic membrane is reduced by the presence of the glycerol in the coupled enzyme reaction series as defined hereinbefore.

The following detailed examples will further illustrate the invention although it should be understood that the invention is not limited to these specific examples.

EXAMPLE

Serum samples containing various levels of triglycerides are incubated with lipolytic enzyme to obtain hydrolysis of the triglycerides as follows:

100 microliters (μl) of the serum sample are admixed with (a) 100 μl of a solution of 120 mg lipase (from *Candida cylindracea*, 540 I.U./mg) in 2 ml of 0.36 M tris buffer, pH 8, and (b) 100 μl of a solution of one ml lipase (from Rhizopus arrhizus, 60,000 I.U./ml) in one ml water. The serum lipase mixture is incubated at 30° C for 30 minutes and retained as the glycerol substrate.

Reagents for the coupled enzyme series of reactions are prepared in aqueous solution as follows:

Buffer Solution 0.1M glycine
0.03M $MgSO_4$
pH 9.9

Enzyme Solution

200 μl GK (from *Candida mycoderma*, 500 I.U./ml)
200 μl α-GPDH (from rabbit muscle, 1400 I.U/ml in 2 Molar $(NH_4)_2 SO_4$ 600 μl H₂O

ATP/NAD Solution 200 mg NAD
100 mg ATP
650 μl H₂O

The buffer solution is deaerated and then reaerated to saturation by stirring at 37° C for 30 minutes.

Two ml. of the aerated buffer solution is then transferred into a cuvette with an attached oxygen-sensing electrode while stirring at about 300 r.p.m. This is followed by the addition of 25 μl of the enzyme solution, 25 μl of the glycerol substrate, 25 μl of an aqueous solution of phenazine methosulfate (one mg./ml.), and 25 μl of the ATP/NAD solution. Maximum reaction rate as determined by the recorder attached to the electrode occurs about 20 seconds after reaction initiation. The relationship of glycerol content in the samples vs. (mv/min.) electrode output was found to be substantially linear.

The oxygen-sensing electrode employed in this example was a modification of the membrane electrode described by Elsworth, The Chemical Engineer, February 1972, pp. 63-71. This modification employed a silver cathode and a lead anode. The electrolyte, which consisted of 5.0M acetic acid, 0.5M sodium acetate and 0.1M lead acetate, instead of being used in a liquid phase as described by Elsworth, was employed in a gelled form by the addition of a small amount of Syton® (Monsanto silica gel) and then applied in film form covered by a Teflon plastic flim.

The electrode was attached to a cuvette, which had an inner Teflon plastic sleeve lining, by entry from the side of the cuvette. The reagents were introduced into the cuvette by entry from the open top. An agitated water bath assembly was employed to maintain a stirring speed of about 300 rpm and a temperature of about 37° C for the reaction components. A Beckman recorder attached to the electrode terminals indicated the electrode output.

Comparisons were made between the results obtained in the above tests and results obtained with a commercially available triglycerides assay kit (Calbiochem Stat Pack) and the data indicated an excellent correlation coefficient of 0.984.

EXAMPLE 2

The procedure of Example 1 is repeated except that a lipase preparation from *Rhizopus delemar* is used instead of the lipase preparation from *Rhizopus arrhizus* with substantially similar results.

Various other examples will be apparent to the person skilled in the art after reading the foregoing disclosure without departing from the spirit and scope of the invention and it is intended that all such examples be included within the scope of the appended claims.

What is claimed is:

1. The method of determining triglycerides in blood serum or plasma comprising reacting a sample of said blood serum or plasma with a lipolytic enzyme to liberate free glycerol, reacting said free glycerol with an oxygenated aqueous solution containing ATP, GK, α-GPDH, NAD and an electron acceptor and measuring the uptake of oxygen by the oxidation of the resulting NADH with an oxygen sensing electrode.

2. The method of claim 1 in which the lipolytic enzyme is a mixture of lipase preparations from *Candida cylindracea* and *Rhizopus arrhizus*.

3. The method of claim 1 in which lipolysis is carried out at a temperature of from about 25° to about 40° C and a pH of from about 7 to about 9.

4. The method of claim 3 in which the pH is maintained by a buffer selected from the group consisting of tris buffer and glycine buffer.

5. The method of claim 1 in which the reaction is carried out at a temperature of from about 25° to about 40° C and a pH of from about 8 to about 10.

6. The method of claim 5 in which the pH is maintained by a buffer selected from the group consisting of tris buffer and glycine buffer.

7. The method of claim 1 in which lipolysis of blood serum or plasma is carried out with a mixture of lipase preparations from *Candida cylindracea* and *Rhizopus arrhizus* at a temperature of from about 25° to about 40° C and a pH of from about 7 to about 9 and in which the reaction is carried out at a temperature of from about 25° to about 40° C and a pH of from about 8 to about 10, said pH ranges being maintained by buffers selected from the group consisting of tris buffers and glycine buffers.

* * * * *